(12) United States Patent
Mudge

(10) Patent No.: US 8,458,149 B2
(45) Date of Patent: Jun. 4, 2013

(54) SMALL FOOTPRINT MEDICAL INFORMATION TRANSFER PROTOCOL STACK

(75) Inventor: Miguel Christopher Mudge, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 561 days.

(21) Appl. No.: 12/749,097

(22) Filed: Mar. 29, 2010

(65) Prior Publication Data

US 2011/0238640 A1    Sep. 29, 2011

(51) Int. Cl.
*G06F 7/00*    (2006.01)

(52) U.S. Cl.
USPC ........... 707/697; 707/699; 714/781; 714/798; 714/799

(58) Field of Classification Search
None
See application file for complete search history.

(56) References Cited

U.S. PATENT DOCUMENTS

| | | | | |
|---|---|---|---|---|
| 5,354,319 | A | * | 10/1994 | Wyborny et al. ............... 607/32 |
| 5,369,649 | A | * | 11/1994 | Murayama et al. ........... 714/781 |
| 6,456,875 | B1 | | 9/2002 | Wilkinson et al. |
| 7,327,732 | B2 | | 2/2008 | Erlenborn |
| 7,369,635 | B2 | | 5/2008 | Spital |
| 7,639,715 | B1 | | 12/2009 | O'Neil |
| 2004/0049246 | A1 | | 3/2004 | Almendinger et al. |
| 2007/0036159 | A1 | | 2/2007 | Pope |
| 2007/0044002 | A1 | | 2/2007 | Johnson |
| 2007/0049990 | A1 | | 3/2007 | Klostermann |
| 2008/0115146 | A1 | | 5/2008 | Claus et al. |
| 2010/0013668 | A1 | | 1/2010 | Kantervik |

FOREIGN PATENT DOCUMENTS

WO    WO 01/80568 A2    10/2001

OTHER PUBLICATIONS

International Search Report and Written Opinion in PCT/US2011/026611 mailed Oct. 27, 2011, 9 pages.

* cited by examiner

*Primary Examiner* — Fred I Ehichioya
*Assistant Examiner* — Hasanul Mobin
(74) *Attorney, Agent, or Firm* — Merchant & Gould P.C.

(57) ABSTRACT

A method of communicating information includes receiving a data stream from the host computer, the data stream including a plurality of bytes, one or more bytes of the plurality of bytes being associated with obtaining medical related information, and parsing one or more bytes in the data stream at the sensor device. As a result of parsing the one or more bytes, the method includes identifying a type of medical related information, obtaining the medical related information from the sensor device, and sending the medical related information to the host computer. The parsing of the one or more bytes in the data stream is performed using a single pass through the data stream, one or more data validity checks being performed during the single pass, the medical related information being obtained after the data stream is parsed in the single pass through the data stream.

18 Claims, 14 Drawing Sheets

SMALL FOOTPRINT MEDICAL INFORMATION TRANSFER PROTOCOL STACK

BACKGROUND

In a medical setting, sensor devices physically attached to a patient are used to monitor the vital signs of a patient. Vital signs that are commonly monitored include blood pressure, temperature, heart rate, oxygen saturation, etc. Medical information obtained from these sensor devices is typically transferred to a patient monitor device, where the information can be processed and displayed.

Medical information transferred between devices typically contains large, high-integrity, highly-defined packets that require a certain level of processing. The packets are typically sent and received through several layers of buffers, each building around the previous. Some medical devices, for example handheld and wireless medical devices, have small processors and typically do not have the processing power required to do extensive packet processing.

SUMMARY

Embodiments of the disclosure are directed to systems and methods for processing medical information transferred to and from medical devices physically attached to a patient.

In one aspect, a method of communicating information from a host computer to a sensor device includes: receiving a data stream from the host computer, the data stream including a plurality of bytes, one or more bytes of the plurality of bytes being associated with obtaining medical related information, one or more of the one or more bytes associated with obtaining medical related information including one or more named fields; parsing one or more bytes in the data stream at the sensor device; as a result of parsing the one or more bytes, identifying a type of medical related information; obtaining the medical related information from the sensor device, the medical related information being obtained using the one or more named fields, the one or more named fields determining a format of the medical related information; and sending the medical related information to the host computer; wherein the parsing of the one or more bytes in the data stream is performed using a single pass through the data stream, one or more data validity checks being performed during the single pass, the medical related information being obtained after the data stream is parsed in the single pass through the data stream.

In another aspect, a first computing device comprises a processing unit and system memory, the memory of the first computing device including instructions that, when executed by the processing unit cause the first computing device to: receive a data stream that includes a plurality of bytes, one or more bytes of the plurality of bytes being associated with obtaining medical related information, one or more of the one or more bytes associated with obtaining medical related information including one or more named fields, parse each byte of the data stream serially, identify metadata relating to actionable data in the data stream, use the metadata to determine where to store the actionable data on the first computing device, after each byte of actionable data is parsed, store the parsed byte of actionable data in a buffer memory on the first computing device, the parsed byte of actionable data being stored in the location of buffer memory indicated by the metadata, use the actionable data in the buffer memory to obtain medical device information at the first computing device, the medical device information being obtained via a sensor included on the first computing device, the medical device information being obtained using the one or more named fields, the one or more named fields determining a format of the medical related information. The actionable data is obtained as a result of a single pass through the data stream received at the first computing device.

In yet another aspect, a computer-readable storage medium comprises instructions that, when executed by a computing device, cause the computing device to: receive a data stream that includes a request for medical device information; use actionable data in the data stream, obtain the requested medical device information at the computing device; serialize the obtained medical device information; and send the serialized medical device information to a host computer.

The details of one or more techniques are set forth in the accompanying drawings and the description below. Other features, objects, and advantages of these techniques will be apparent from the description, drawings, and claims.

DETAILED DESCRIPTION

The present disclosure is directed to systems and methods for processing medical information transferred to and from medical devices physically attached to a patient. In some examples, the medical information is processed on a byte-by-byte basis without extensive buffer processing and without the use of an operating system. The systems and methods provide a streamlined, small-footprint approach to processing medical device information. The systems and methods implement a small-footprint communication protocol, also known as a communications stack.

Each medical device includes a processor that implements a state-based software program used to process the medical information. The medical information is included in packets of data received by and sent from each medical device. For each packet of data, the software program categorizes the data into structure, integrity and actionable data. The software program parses each byte of data to determine the structure of the data and to organize storage for the actionable data.

Actionable data is data that the software program can use to obtain the medical information. Actionable data includes commands and parameters associated with commands. An example command is TEMP. An example parameter is degrees Fahrenheit (° F.). Bytes that involve actionable data are stored until the complete packet is parsed and the integrity of all bytes in the packet are verified.

The actionable data typically includes a command issued from a host computer. For example, the host computer may request a temperature reading from a patient. Application software included on the medical device processes the actionable data, obtains the requested information, for example the temperature of the patient, from the medical device and sends a response with the requested information back to the host computer.

The software program processes the packet data using a single pass over the packet data in which each byte of packet data is processed serially. Using a single pass provides speed advantages over software protocol parsers that copy the entire packet into a buffer and make several passes over the buffer in order to process elements in the packet data. The use of a single pass reduces processing latency. It is also possible for the medical device to receive a second data packet at the same time as a first data packet is being processed.

Figure 1:
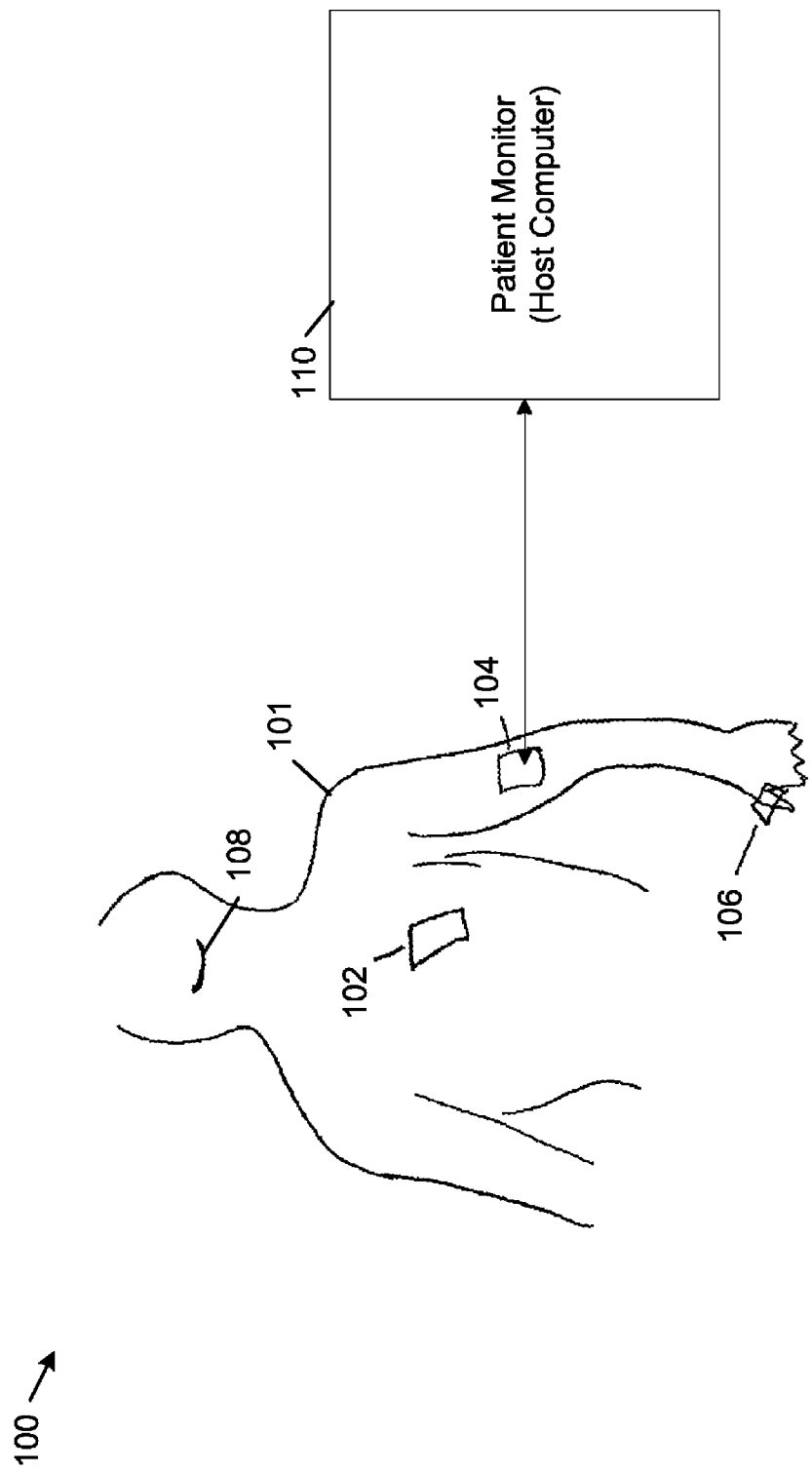
FIG. 1 shows an example system that includes a small footprint medical sensor device and a patient monitor.

FIG. 1 shows an example system 100 that implements a small-footprint method of processing medical device information. FIG. 1 shows a plurality of example medical sensor devices 102, 104, 106, 108 physically attached to a patient 101. In example system 100, device 102 is an ECG sensor used to measure heart function as part of during an electrocardiogram, device 104 is a blood pressure sensor, device 106 is an $SPO_2$ sensor that measures oxygen saturation and device 108 is a thermometer that measures the temperature of the patient. Alternatively, device 108 may be a temperature sensor that is attached to the patient, for example to an ear. For the purposes of this disclosure, device 108 is considered to be a temperature sensor. Other medical devices are possible.

Also shown in FIG. 1 is an example patient monitor 110 that receives medical information from devices 102, 104, 106, 108 processes the medical information and displays the medical information. The example patient monitor 110 also sends request for medical information to devices 102, 104, 106, 108. The patient monitor 110 is a computing device. For the purposes of this disclosure, the patient monitor 110 is considered to be a host computer. In this disclosure patient monitor 110 and host computer 110 are used interchangeably.

The medical sensor devices 102, 104, 106, 108 may be physically attached to patient monitor 110, typically via a USB connection to patient monitor 110 or the medical sensor devices may be attached to patient monitor 110 via a wireless connection. An example wireless connection is one that uses Bluetooth wireless technology. In example system 100, blood patient monitor 104 is physically attached to patient monitor 110 and ECG sensor 102, $SPO_2$ sensor 106 and temperature sensor 108 are connected to patient monitor 110 using Bluetooth.

Figure 2:
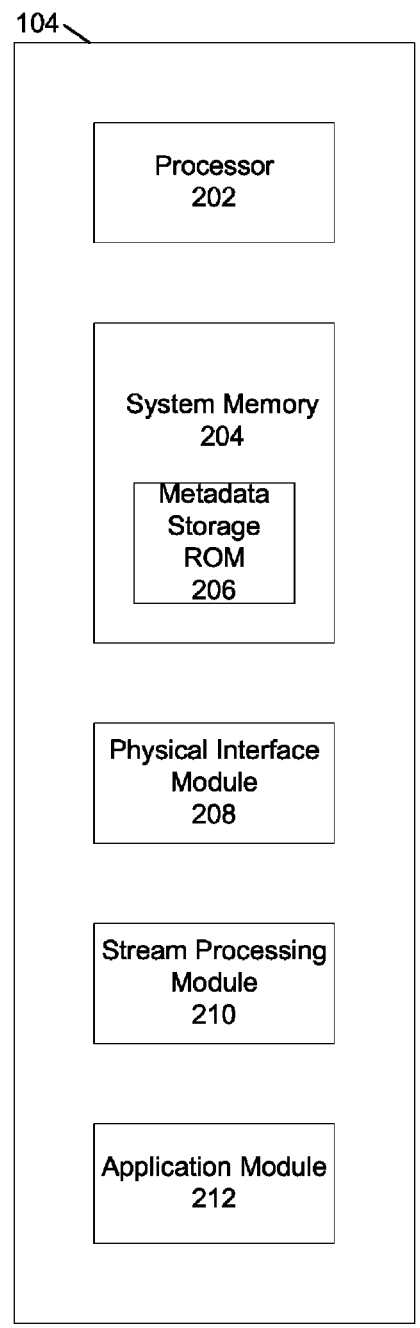
FIG. 2 shows example modules of an example small footprint medical sensor device of FIG. 1.

FIG. 2 shows example modules included in blood pressure monitor device 104. These same example modules are also included in example ECG sensor device 102, $SPO_2$ sensor device 106 and temperature sensor 108. The example device 104 includes a processor 202, system memory 204, metadata storage ROM 206, physical interface module 208, stream processing module 210 and application module 212.

The processor 202 is a computing device that includes instructions for processing data received from and sent to host computer 110 and instructions for processing medical device information on device 104. The system memory 204 may be volatile (such as RAM), non-volatile (such as ROM, flash memory, etc.) or some combination of the two. However, because data is processed on device 104 in a simplified manner, one-byte at a time, because actionable is moved directly from an incoming data stream to a single static buffer and because actionable data is organized as it arrives so that dynamic memory allocation is not needed, an operating system is not required and system memory 204 does not typically require an operating system. The system memory also includes one or more software applications for processing requests for medical device information and may include program data. The processor 202 and system memory 204 are typically part of a microcontroller included in device 104, wherein the system memory 204 is internal memory on the microcontroller. A typical medical sensor device 102, 104, 106, 108 ranges from 0.014 to 0.06 square inches in size.

The example system memory 204 includes a read only memory (ROM) 206 that stores metadata. The metadata stored in metadata storage ROM 206 is used to process data received from and sent to host computer 110. The metadata is generated once by an application program, typically run on a personal computer, based on a hardware abstraction of the sensor device being used, for example sensor device 102, 104, 106, 108, etc. The metadata generated by the application program is stored in metadata storage ROM 206 on the sensor device being used, for example sensor device 104.

Data is received from host computer 110 in a serial data stream. The metadata stored in metadata storage ROM 206 facilitates the deserialization of incoming data in the data stream and the serialization of outgoing data. The metadata is typically stored in a C programming language structure that includes version and type information, information about static and dynamic variables in the data stream and information about any objects in the data stream. The metadata describes how to move data from the stream to the C structure and back.

The objects include fields that identify the type and structure of medical information to be obtained from sensor device 104. Example objects include structure for medical information to be obtained, such as temperature, blood pressure, etc. A separate object is used for each type of medical information. Other example objects include patient identification, clinician identification and time and date information.

The example physical interface module 208 provides a physical interface that receives messages from host computer 110 and that sends responses to host computer 110. The messages are in the form of packets that include an envelope, a message and optionally one or more objects with medical device information.

The example stream processing module 210 processes the incoming and outgoing packets, deserializing information in the incoming packets and serializing information in the outgoing packets. Using metadata provided by metadata storage ROM 206, the stream processing module 210 writes actionable data included in the incoming packet into buffer memory area on sensor device 104.

The example application module 212 processes actionable data included in the incoming packet and obtains medical information from a sensor device. For example, for sensor device 104, the application module 212 initiates a blood pressure cuff inflation process and obtains blood pressure readings from sensor device 104. For sensor device 108, the application module 212 obtains temperature readings from sensor device 108.

Figure 3:
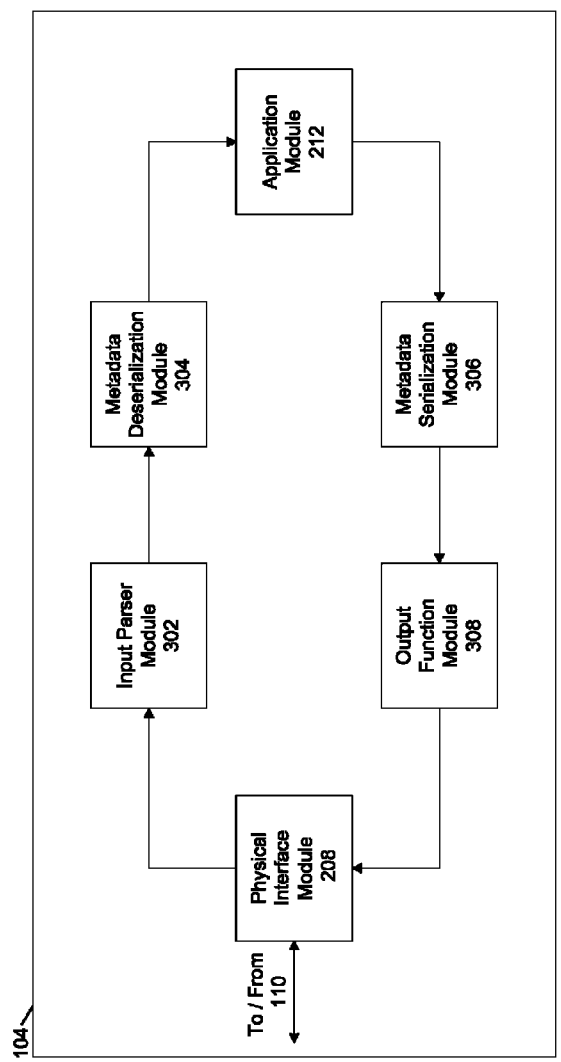
FIG. 3 shows an example architecture of a small footprint medical sensor device that includes the modules of FIG. 2.

FIG. 3 shows modules used in an example architecture for blood pressure monitor sensor device 104. These same example modules are also included in example ECG sensor device 102, $SPO_2$ sensor device 106 and temperature sensor 108. The example sensor device 104 includes a physical interface module 208, input parser module 302, metadata deserialization module 304, application module 208, metadata serialization module 306 and output function module 308. The example input parser module 302, metadata serialization module 304, metadata serialization module 306 and output function module 308 are part of the example stream processing module 210.

The example physical interface module 208 includes circuitry to send and receive packet data. Packet data is typically received from patient monitor 110 when patient monitor 110 requests an update of sensor data, for example when patient monitor 110 requests a blood pressure reading. Packet data is sent from sensor device 104 when sensor device 104 obtains a blood pressure reading on patient 101 and sends the obtained blood pressure reading to patient monitor 110. Once a request for a blood pressure reading is received by sensor device 104, sensor device 104 may send a plurality of blood pressure readings to patient monitor 110 so that the progress of the blood pressure reading is displayed.

The physical interface module 208 implements I/O commands such as data stream reads, data stream writes, and data stream flushing. A data stream comprises a string of bytes read from or written to the packet data. A data stream flush is accomplished at the end of every complete message.

The example input parser module 302 parses the input stream of packet data sent from example patient monitor 110. One byte is parsed at a time. The packet data conforms to a medical device communication protocol that defines the format of data within the packet. The packet includes header fields that specify the meaning of bytes that follow in the packet, that specify the size and structure of actionable data bytes in the packet and that specify the point at which the actionable data bytes start in the packet.

The packet also includes the actionable data bytes. In the input stream of packet data, the actionable data bytes represent a command sent from the example patient monitor 110 for patient information. For example, the actionable data bytes may includes a string of bytes requesting the blood pressure of patient 101 from sensor device 104. As another example, the actionable data bytes may include a string of bytes requesting the temperature of the patient in degrees Fahrenheit. Temperature sensor 108 provides the temperature of the patient. The specific details of how the input parser module parses data in the input stream is discussed later on in this specification.

The example metadata deserialization module 304 receives each byte of actionable data, stores each byte in a data buffer and performs a data integrity check, typically a CRC (cyclic redundancy check) calculation on the data. The metadata deserialization module 304 uses data type flags obtained from metadata stored by metadata storage ROM 206 to determine the structure of the actionable data. The specific details of how this is accomplished are discussed later on in this specification.

The example application module 212 implements the action specified by the actionable data stored. For example, if the action specified is to obtain a blood pressure reading from patient 101, the application module 212 initiates a blood pressure read operation and monitors the example blood pressure sensor device 104 for blood pressure readings. A blood pressure read operation includes pressuring and then depressurizing a blood pressure cuff on the arm of the patient. As the cuff inflates, the application module 212 obtains blood pressure readings from sensor device 104.

At a predetermined sampling time, the application module 212 sends each obtained blood pressure reading to the example metadata serialization module 306 so that the blood pressure reading can be sent to patient monitor 110 and displayed. When the blood pressure operation is completed, the application module 212 calculates the systolic and the diastolic blood pressure for the patient and sends bytes corresponding to the systolic and diastolic blood pressure to the metadata serialization module 306.

The example metadata serialization module 306 receives one or bytes of data from the application module and serializes this data so that it can be returned to example patient monitor 110. For example, during a blood pressure measurement operation, bytes corresponding to each sample of blood pressure readings are serialized. Similarly, at the completion of the blood pressure measurement operation, bytes corresponding to the systolic and diastolic blood pressure of the patient are serialized. The specific details of how serialization is accomplished are discussed later on in this disclosure.

The example output function module 308 receives data bytes from the application module 212 corresponding to operation performed, for example the results of a blood pressure reading and incorporates the received data bytes into an output packet. The output function module 308 provides an envelope for the received data and includes the required format expected by the patient monitor 110.

When the output packet is completed, the output function module 308 sends the output packet to the physical interface module 208. The physical interface module 208 sends the output packet to patient monitor 110.

Figure 4:
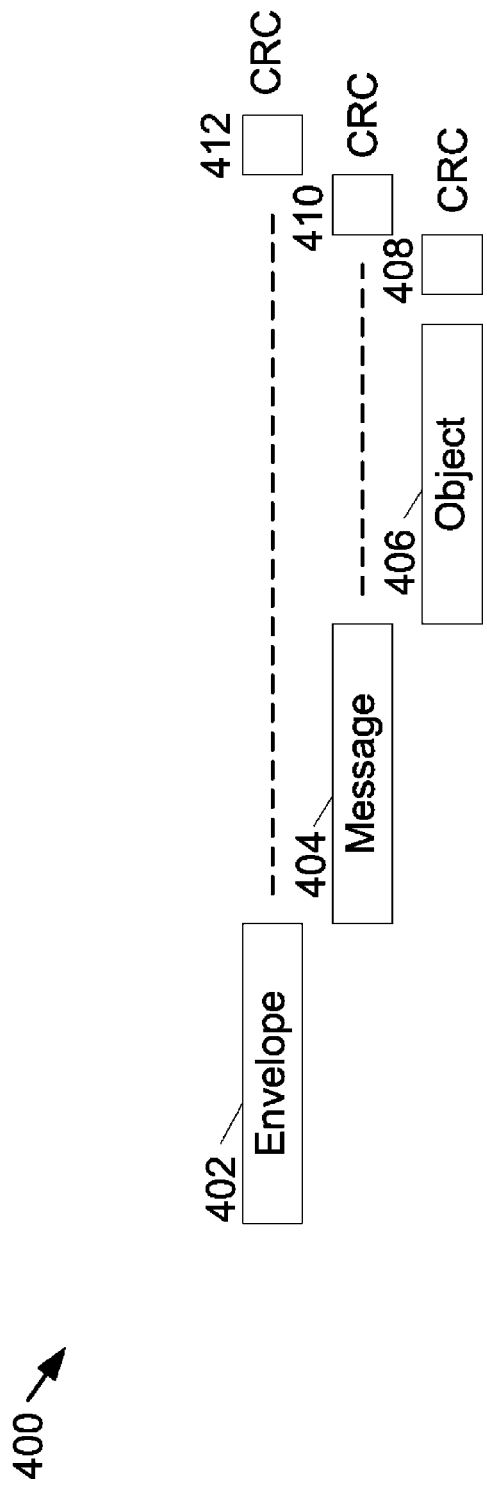
FIG. 4 shows an example structure of a data packet used in transmitting medical information.

FIG. 4 shows the structure of an example packet 400 of input data that is consistent with the medical device communication protocol discussed in this disclosure. FIG. 4 shows that each packet includes three sections, an envelope section 402, a message section 404 and an object section 406. In addition, a CRC 408 is included at the end of object section 406, a CRC 410 is included at the end of message section 404 and a CRC 412 is included at the end of envelope section 402.

Each CRC 408, 410, 412 is a 2-byte field that stores a cyclic redundancy check (CRC) used to verify the data integrity of the corresponding packet section—envelope, message and object. As explained later in this document, separate CRC calculations are performed for the envelope section 402, the message section 404 and the object section 406. For each CRC calculation, the CRC is stored in a separate 2-byte area of memory, typically 2-bytes in an array.

Figure 5:
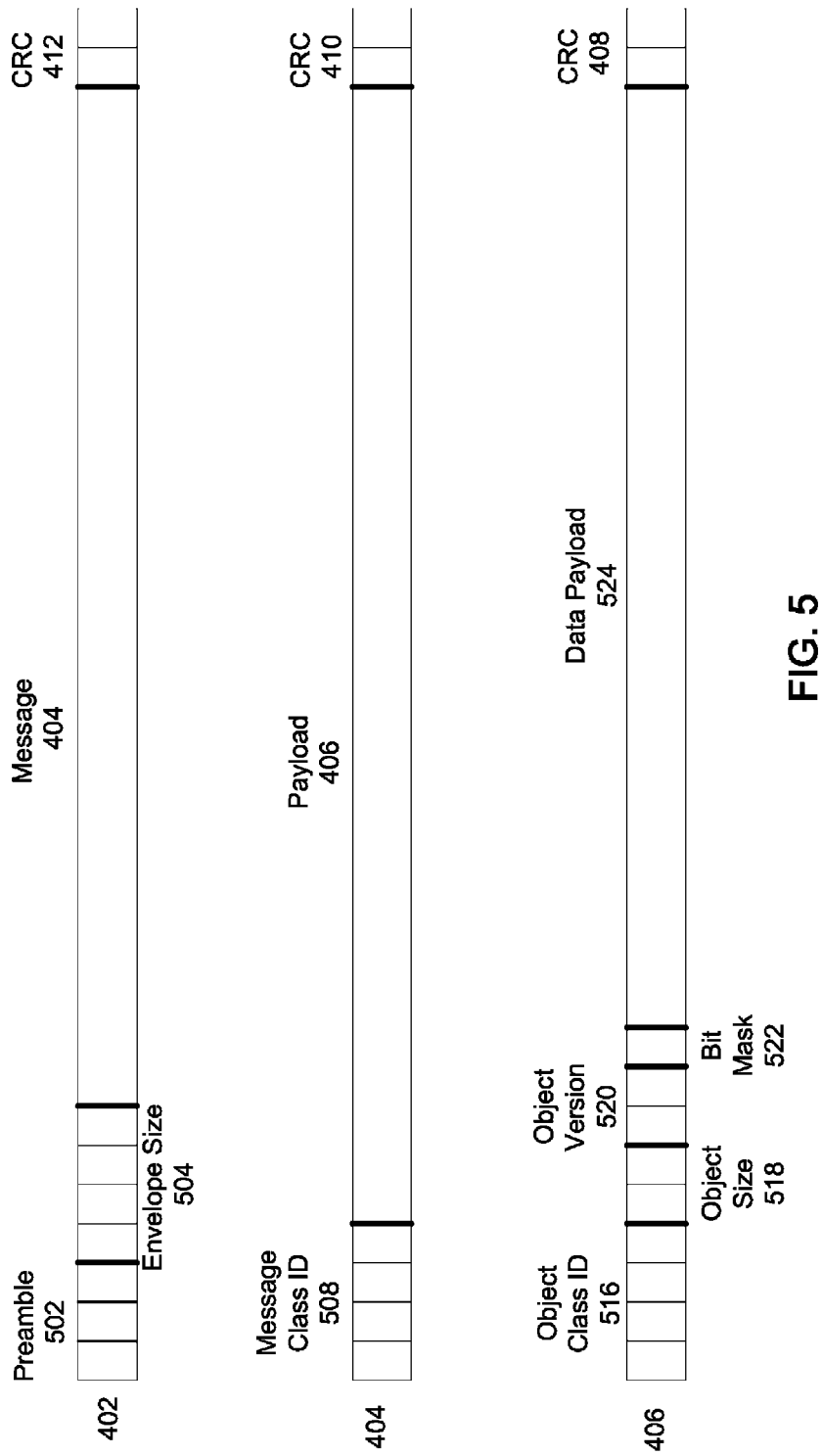
FIG. 5 shows example data formats for the envelope, message and object shown in FIG. 4.

FIG. 5 shows the sections of the example packet 400 in more detail. The example envelope section 402 includes a preamble section 502, packet length bytes 504, and message section 404, followed by CRC 412. In the example shown in FIG. 5, the preamble section 502 includes a 3-byte preamble. However, more or fewer bytes may be included in the preamble. Each of the preamble bytes determines an internal state of operation. Thus, the first preamble byte corresponds to state 1, the second preamble byte corresponds to state 2 and the third preamble byte corresponds to state 3. The preamble bytes are preprogrammed so they can be recognized by input parser module 302. In one example, the first preamble byte is CNTL W, the second preamble byte is CNTL A and the third preamble byte is CTNL L. Other examples are possible.

Following the preamble bytes is a four-byte field 504 that represents the size of the envelope section 402. Reaching field 504 corresponds to state 4. Following the field 504 is the start of message 404.

The details of message 404 are shown in the center section of FIG. 5. The example message section 404 includes a message class ID 508 and payload 406, followed by CRC 410. The example message class ID 508 is a 4-byte field corresponding to a specific message class. The CRC 410 represents a calculated CRC for the sum of the bytes in message section 404.

The example message class ID 508 includes a family, a genus and a species. The family represents the purpose of the data, the genus represents an action (for example a request, response, command, etc.) and the species represents a specific type of operation (for example, get the name of a clinician or start a non-invasive blood pressure (NIBP) operation or obtain a blood pressure reading from a patient.

The species represents a named field corresponding to the type of information requested, for example, the name of the clinician or a blood pressure reading. The named field permits application module 212 to determine a format for the requested information, permitting application module 212 to obtain the requested information without any additional data conversion or processing. For example, a species of GET-CLINICIAN indicates that the name of the clinician is to be returned as one or more characters. As another example, a species of GET_BP indicates that the blood pressure is to be returned as one or more numbers.

In some examples payload 406 corresponds to object 406 in FIG. 4. This is for the case where there is only one object included in example packet 400. However, in other examples, packet 400 may have one or more additional objects embedded in payload 406. Typically, there is not more than one object embedded within an object.

Object 406 is a medical device object that includes specific medical information. In examples, object 406 may include a patient's name, identification number, a clinician's name and identification number, and a time stamp. Object 406 may also include an identifier representing the type of information requested, such as temperature, systolic blood pressure, diastolic blood pressure, mean arterial pressure, heart rate, oxygen saturation, etc. Other types of information are possible.

The details of object 406 are shown in the bottom section of FIG. 5. The example object 406 includes object class ID 516, object size 518, object version 520, bit mask 522 and data payload 524, followed by CRC 408. The example object class ID 516 is a 4-byte field corresponding to a specific object class.

Two example object classes are CNIBPDStd and CDeviceDStd. The example CNIBPDStd class belongs to the family for non-invasive blood pressure (FmNIBP), and includes members for systolic blood pressure, diastolic blood pressure, and mean arterial pressure, heart rate, status flags and a time stamp. The example CDeviceDStd class belongs to the family for device (FmDEVICE) and includes information about the device, including the model name, serial number, etc.

The object size 518 is the size of object field 406, the object version 520 is a version identifier for object 406 and bit mask field 520 is a one-byte bit mask associated with object 406. The data payload represents a static or dynamic payload. The CRC 408 represents a calculated CRC for the sum of the bytes in object section 406.

Figure 6:
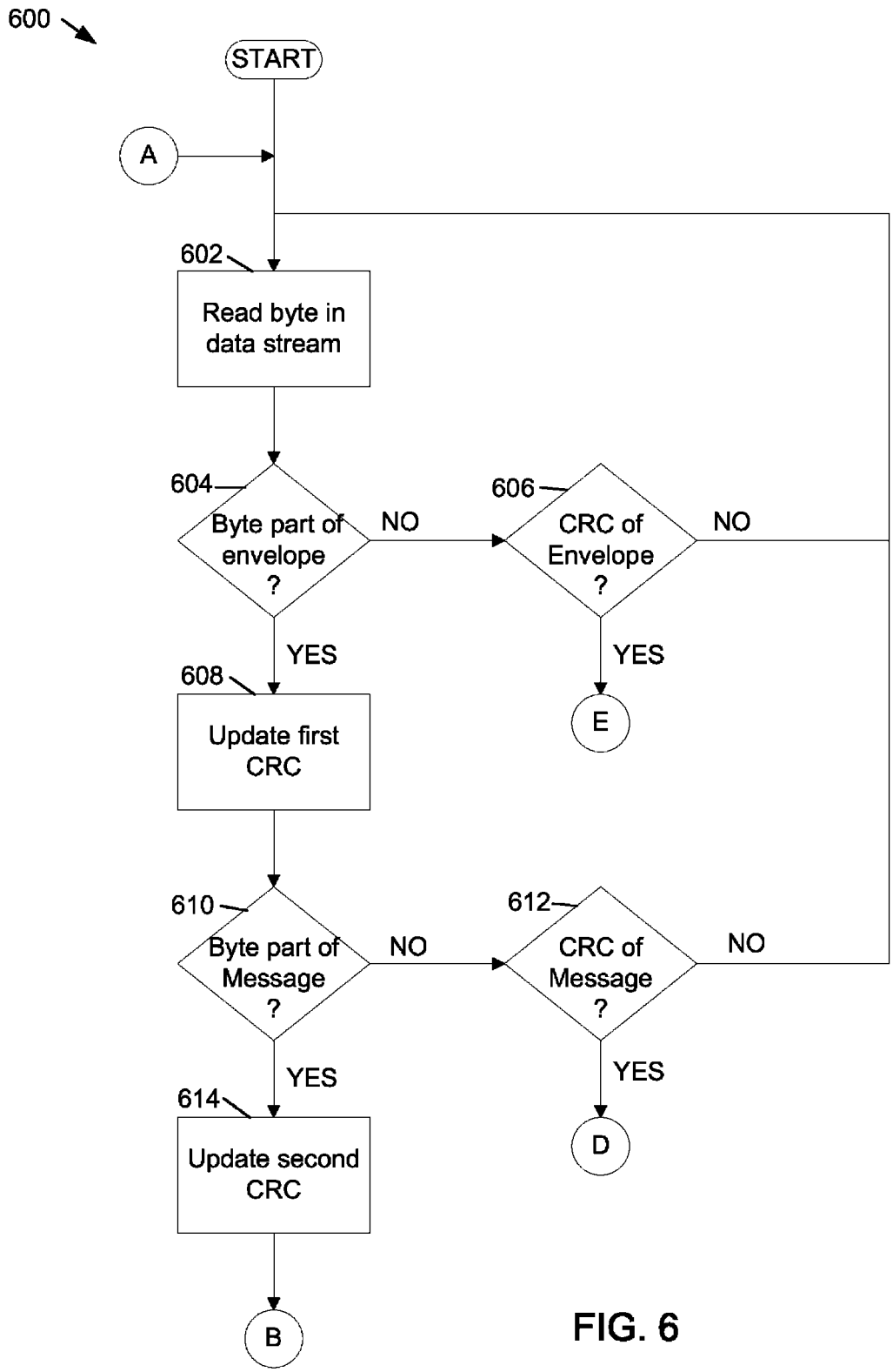
FIGS. 6, 7 and 8 show a flow chart of a method for processing a data packet that includes medical device information.
Figure 7:
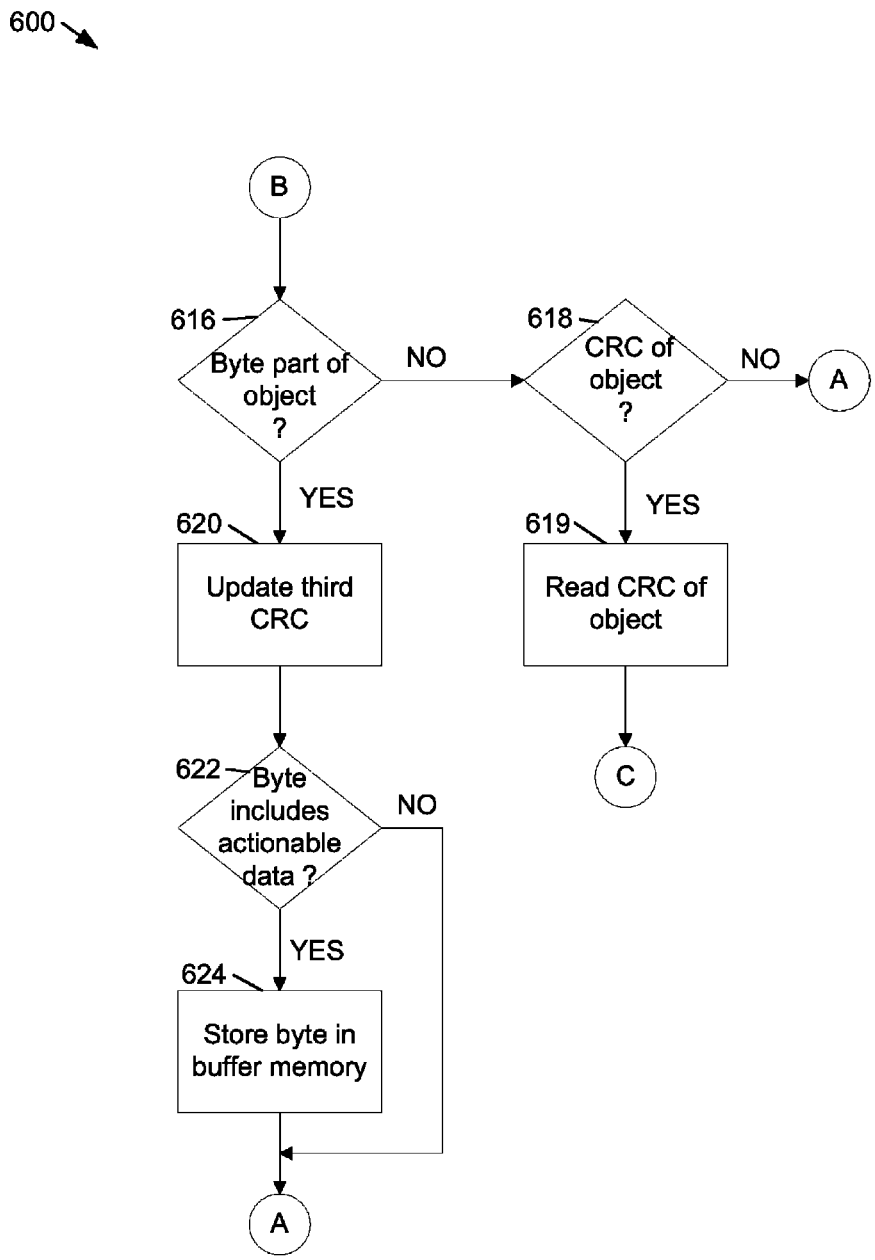
Figure 8:
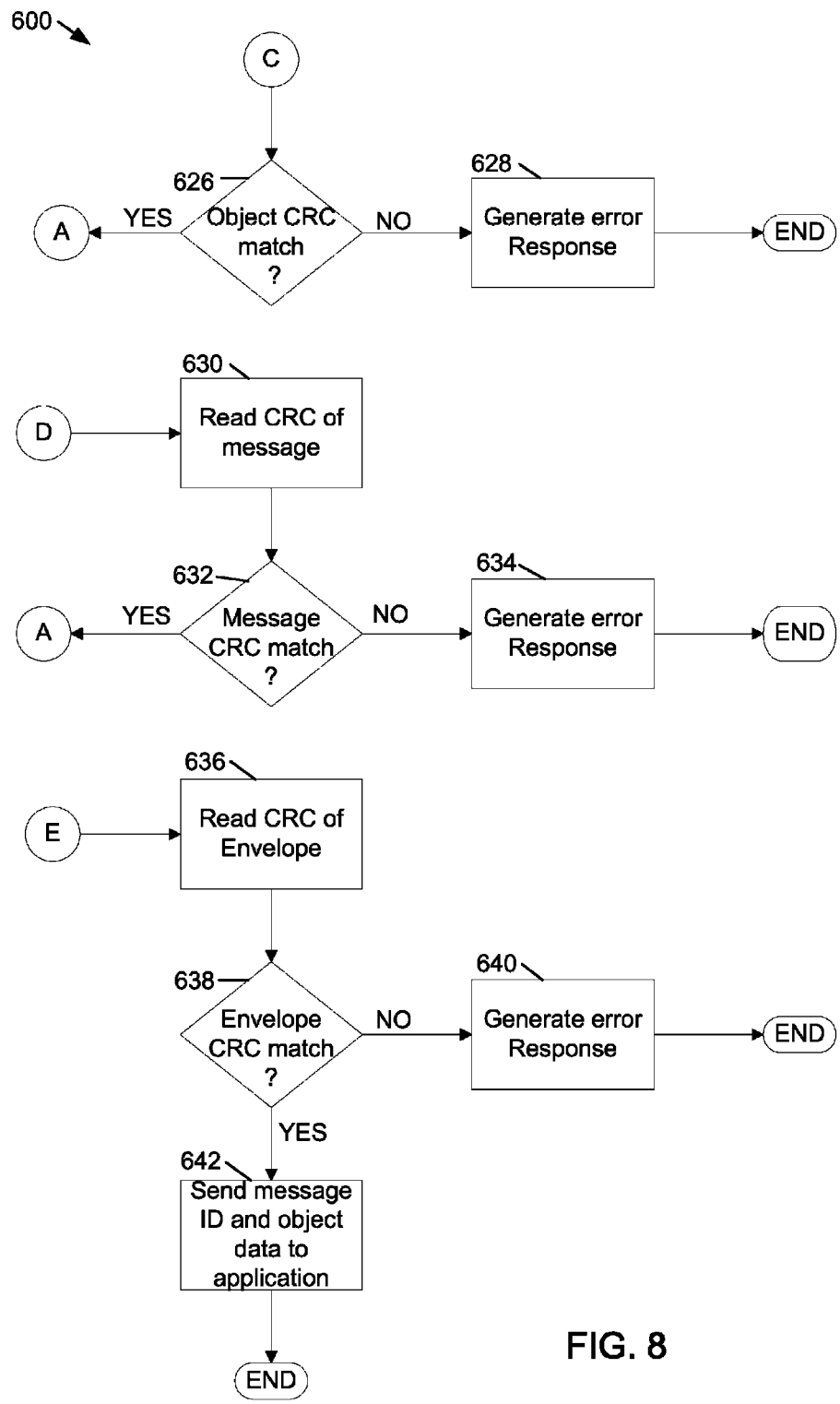

FIGS. 6, 7 and 8 show an example method 600 for processing a data packet that includes medical device information. The example data packet is sent from a host computer, for example a host computer included in patient monitor 110 and the data packet is processed on a medical device, for example on blood pressure monitoring device 104. The example blood pressure monitoring device 104 contains electronic components, including a processor and memory, which are used to process the data packet. The processing is done in streamlined fashion, without the use of an operating system and by performing a single pass over the packet data.

At operation 602, the processor reads a byte in the packet data stream. At operation 604, a determination is made as to whether the byte read at operation 602 is part of the envelope 402. As shown in FIG. 4, the envelope 402 includes the message 404, the object 406, object CRC 408 and message CRC 410. However, the envelope 402 does not include the envelope CRC 412. When a determination is made at operation 604 that the byte read at operation 602 is not part of the envelope, at operation 606 a determination is made as to whether the byte read at operation 602 is part of the envelope CRC 412. When it is determined at operation 606 that the byte read at operation 602 is part of the envelope CRC 412, control passes to operation 636, as discussed later in this disclosure. When it is determined at operation 606 that the byte read at operation 602 is not part of envelope CRC 412, meaning that the byte read at operation 602 is an unexpected byte, the byte is discarded and control passes to operation 602 where another byte is read in the packet data stream.

When it is determined at operation 604 that the byte read at operation 602 is part of the envelope 402, at operation 608 a first CRC is updated. The first CRC is a 16-bit number stored in a first area of memory, typically two bytes in an array, dedicated to perform an integrity check on the envelope 402 portion of the packet data. For the example method 600, the envelope portion 402 of the packet data includes the preamble 502, the envelope size 504 and the message 404. When the first CRC is updated, the first CRC is recalculated to include the byte read at operation 602.

At operation 610, a determination is made whether the byte read at operation 602 is part of message 404. A byte that is part of message 404 includes any byte within the message class ID 508 or message payload 406, but does not include message CRC 410. When it is determined that the byte read at operation 602 is not part of message 404, at operation 612 a determination is made as to whether the byte read at operation 602 is part of the message CRC 410. When it is determined at operation 606 that the byte read at operation 602 is part of the message CRC 410, control passes to operation 630, as discussed later in this disclosure. When it is determined at operation 612 that the byte read at operation 602 is not a part of the message CRC 410, control passes to operation 602 and another byte is read from the data stream.

When it is determined at operation 610 that the byte read at operation 602 is part of the message 404, at operation 614, a second CRC is updated. The second CRC is a 16-bit number stored in a second area of memory, typically two bytes in an array, dedicated to perform an integrity check on the message 404 portion of the packet data. For the example method 600, the message 404 portion of the packet data includes the message class ID 508 and the payload 406. The second area of memory is different than the first area of memory, typically a separate row in the array. When the second CRC is updated, the second CRC is recalculated to include the byte read at operation 602.

At operation 616, a determination is made as to whether the byte read at operation 602 is part of object 406. A byte that is part of object 406 includes any byte within the object 406, but does not include object CRC 408. When it is determined that the byte read at operation 602 is not part of object 406, at operation 618 a determination is made as to whether the byte read at operation 602 is part of the object CRC 408. When it is determined at operation 618 that the byte read at operation 602 is part of the object CRC 408, at operation 619, the object CRC 408 is read from the packet data stream. Control then passes to operation 626, as discussed later in this disclosure. When it is determined at operation 618 that the byte read at operation 602 is not a part of the object CRC 408, control passes to operation 602 and another byte is read from the data stream.

When it is determined at operation 616 that the byte read at operation 602 is part of the object 406, at operation 620, a third CRC is updated. The third CRC is a 16-bit number stored in a third area of memory, typically two bytes in an array, dedicated to perform an integrity check on the object 406 portion of the packet data. For the example method 600, the object 406 portion of the packet data includes the object class ID 516, the object size 518, the object version 520, the bit mask 522 and the data payload 524. The third area of memory is different than the first and second areas of memory, typically a separate row in the array. When the third CRC is updated, the third CRC is recalculated to include the byte read at operation 602.

At operation 622, a determination is made as to whether the byte read at operation 602 includes actionable data. Most bytes of object 406 include actionable data, with the exception of certain status bytes and similar non-actionable bytes. When it determined at operation 622 that the byte read at operation 602 includes actionable data, at operation 624 the byte read at operation 602 is stored in buffer memory. Buffer memory is typically a static memory area of device 102, 104, 106, 108 that stores the actionable bytes in object 406. Control then passes to operation 602 and another byte is read from the packet data stream. When it is determined at operation 622 that the byte read at operation 602 does not include actionable data, the byte read at operation 602 is not stored in buffer memory. Instead, control passes to operation 602 and another byte is read from the packet data stream.

At operation 626, a determination is made as to whether the object CRC 408 read from the packet data stream matches the third CRC. When the object CRC 408 matches the third CRC, validating the integrity of data within object 406, control passes to operation 602 and another byte is read from the packet data stream. When the object CRC 408 does not match the third CRC, at operation 628 an error response is generated and the data packet processing operation ends.

At operation 612 when a determination is made that the byte read at operation 602 is part of the message CRC 410, at operation 630 the message CRC 410 is read from the packet data stream. At operation 632, a determination is made whether the message CRC 410 read from the packet data stream matches the second CRC. When the message CRC 410 matches the second CRC, validating the integrity of data within message 404, control passes to operation 602 and another byte is read from the packet data stream. When the message CRC 410 does not match the second CRC, at operation 634 an error response is generated and the data packet processing operation ends.

At operation 606 when a determination is made that the byte read at operation 602 is part of the envelope CRC 412, at operation 636 the envelope CRC 412 is read from the packet data stream. At operation 638, a determination is made whether the envelope CRC 412 read from the packet data stream matches the first CRC. When the message CRC 410 matches the first CRC, validating the integrity of data within envelope 402, at operation 642 message class ID 508 and the data object stored in buffer memory are sent to application module 212 for processing. When the envelope CRC 412 does not match the first CRC, at operation 640 an error response is generated and the data packet processing operation ends.

The example method 600 illustrated in FIGS. 6, 7 and 8 describes a process in which CRC checks are performed for three sections of the incoming data packet—the envelope 402, the message 404 and the object 406. However, in examples there may be one or more additional objects embedded in object 406, depending on the type of medical device information being requested. For the examples where there are objects embedded within objects, an additional CRC check is performed for each embedded object. The CRC for each additional CRC check is stored in a separate area of memory, typically a separate row in the array that stores the CRCs for the envelope 402, message 404 and object 406. Typically, because of space and processing considerations, not more than one object is embedded in object 406.

Figure 9:
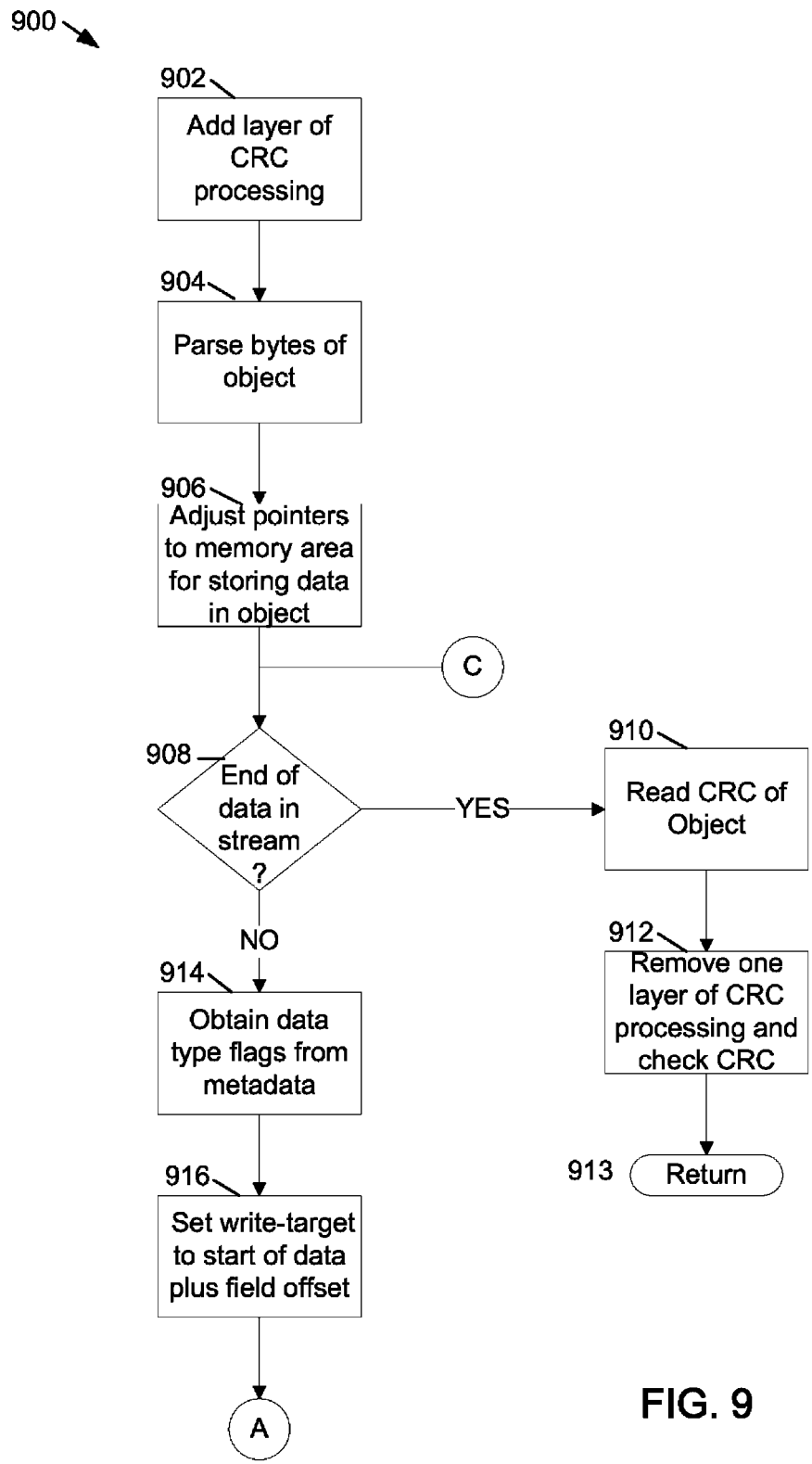
FIGS. 9, 10 and 11 show an example method for deserializing metadata in an object.
Figure 10:
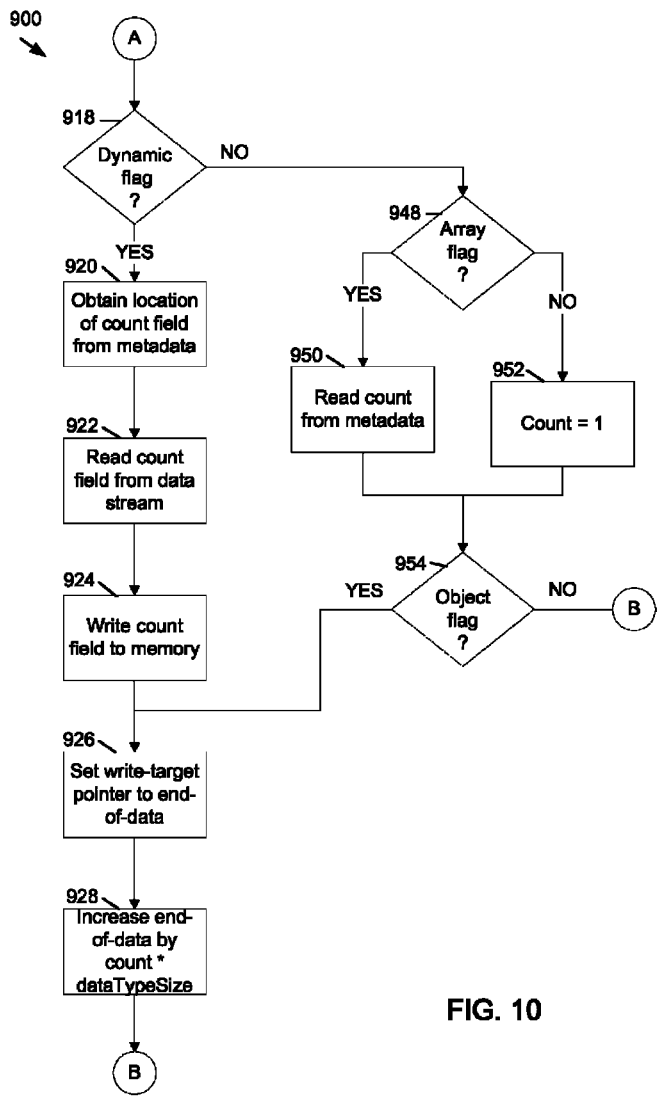
Figure 11:
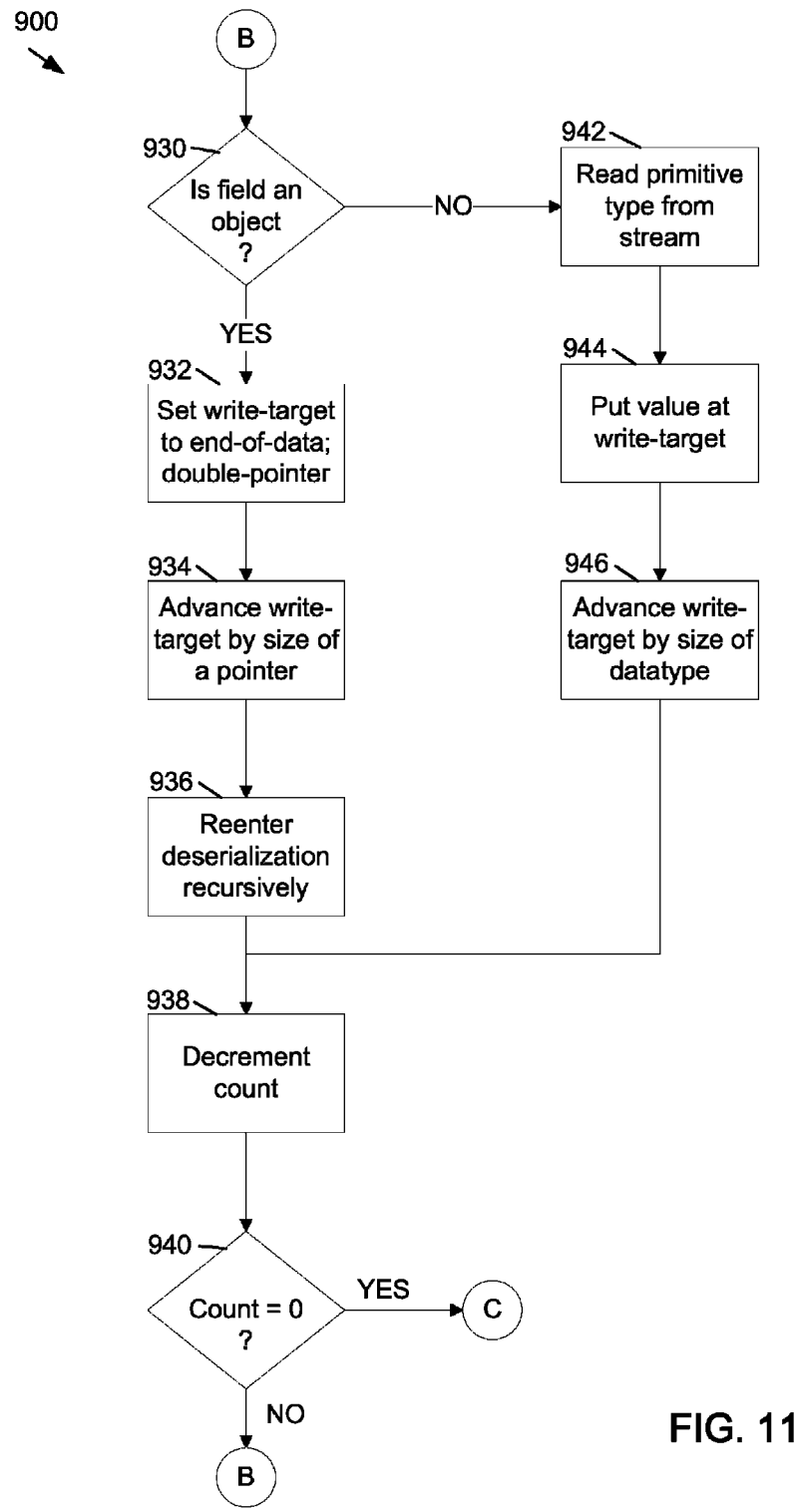

FIGS. 9, 10 and 11 show an example method 1000 for deserializing data in an object, for example object 406. Method 900 starts when a byte read from the received packet data is identified as being part of object 406. At operation 902, a layer of CRC processing is added and a CRC count is incremented for object 406. The CRC count represents the number of CRC calculations performed during packet processing, so one additional a count is being added at operation 902 for object 406.

At operation 904, a byte of object 406 is parsed. The first bytes of object 406 comprise header information and typically indicate the type of object, for example via object class ID 516, the size of the object, for example by object size 518, a version of the object, for example via object version 520 and information about the object, for example via information included in object class ID 516. The header information in object 406 is not stored in memory because it is not needed by the application.

As each byte of data in the object 406 is parsed, at operation 906 pointers are adjusted to point to the start of a buffer memory and to point to a location in the buffer memory corresponding to an end of data. The buffer memory is the area of memory in which the data payload of object 406, for example data payload 524, is to be stored. The buffer memory for storing the data payload is variable in size because different objects have different memory requirements.

The start of the buffer memory is the first location of buffer memory that stores data payload 524. The pointer corresponding to the end of data is the start of the buffer memory plus the size of a static structure obtained from metadata stored in metadata storage ROM 206. The static structure represents static variables that are included in the object. An example of a static variable is a patient's name or identification number. The pointer to end of data points to the buffer memory following the end of the static variables included in the object. This provides a pointer for storing any additional data that may be included in the packet following the end of the static variables.

At operation 908, a determination is made as to whether the end of data in the data stream for the object 406 has been reached. When it is determined that the end of data has not been reached, at operation 914, data type flags are obtained from the metadata. For example, the data type flags may specify that the data type is an integer, 4-bytes in length.

At operation 916, a write-target is set equal to the start of data plus a field offset obtained from the metadata. The write target provides an indication to the application where specific fields in the packet data are located. For example, for a first data field in the packet data, the offset is zero, so that that first field, for example a static variable, is written to buffer memory at the start of data. However, for a second data field, for example, a second static variable, if the data type is an integer, the write-target is offset four-bytes from the start of data, since an integer, in this example, is 4-bytes long.

At operation 918, a determination is made as to whether the object includes dynamic data. When the object includes dynamic data a dynamic flag is set in the metadata. For dynamic data, the amount of the dynamic data is determined by a host computer, for example the host computer at patient monitor 110. The host specifies how many numbers or letters or objects are included in the data. For example, if the data is a wave, the data may include a variable number of samples, for example 10 samples or 100 samples. For static data, the amount of static data is determined from the metadata.

When it is determined that a dynamic flag is set, at operation 920, the location of a count field is obtained from the metadata. The count field specifies the number of samples of a dynamic type of medical information that are included in the data packet. For example, the count field may specify the number of samples of temperature data or the number of samples of a wave function.

At operation 922 the count field is read from the packet data stream and at operation 924, the count field is stored in memory. Typically, the count field is included in the packet data stream immediately preceding the dynamic medical information, for example before the samples of temperature data, etc. At operation 926, a write-target pointer is set to the end of data and stored in memory. The end of data is the current end of data as determined in operation 906. To take into account the dynamic data, at operation 928, the end of data is increased by the value of the count field multiplied by the data type size. For example, if the count indicates that there are 5 bytes of dynamic data, each byte being an integer 4-bytes in length, the end of data is increased by 20 bytes and the write target is set to this new end of data.

When it is determined at operation 918 that the metadata does not include a dynamic field, at operation 948, a determination is made as to whether the metadata includes an array field. For example, if the object includes the name of a patient, the name may be stored in an array of characters. When an object includes an array field an array flag is set in the metadata. When it is determined that the object 406 includes an array flag, at operation 950 the count of array elements is read from the metadata. For example, the metadata may specify the number of characters in the array. When it is determined at operation 950 that the array flag is not set, at operation the count of array elements is set to 1.

At operation 954, a determination is made as to whether an object flag is set. The object flag indicates whether one object is embedded in a second object. An example of one object being imbedded in a second object is a temperature object, representing the temperature of a patient, embedded in an object including a scanned bar code for the patient. In examples, the bar code object may be embedded in the temperature object. The object flag is set in the metadata for an object. When a determination is made that the object flag is set, for example by evaluating the metadata, at operation 926, a write-target is set to the end of data and at operation 928, the end of data is increased by a count representing the number of objects multiplied by a data type size representing the size of each object. The write-target is a pointer that keeps track of the next free memory location. When actionable data, such as a number, is read from the data stream, the actionable data is written to the memory location pointed to by the write-target.

At operation 930, a determination is made whether the current field is an object. If the current field is not an object, at operation 942, a primitive type is read from the packet data stream. A primitive type can be either a character or a number. At operation 944, the primitive type is stored in memory at the location pointed to by the write target. At operation 946, the write target is advanced by the size of the data type, for example by 4-bytes for an integer and by one-byte for a character.

At operation 938, the count set earlier is decremented by one. Then, at operation 942, a determination is made as to whether the count is equal to zero. If a determination is made that the count is equal to zero, control proceeds to operation 908, and if the end of data is not reached, another byte of packet data is processed. However, if a determination is made at operation 942 that the count is not zero, control proceeds to operation 930 and a determination is made whether the current field is an object. The count is not zero if there are more bytes of an array, more dynamic bytes or more embedded objects to process, as determined by the count read at operations 950 and 922 for arrays and dynamic elements, respectively. Typically, only one object is embedded.

At operation, 930, when a determination is made that the field is an object, a pointer is set to point to the write-target that points to the end of data, resulting in a double pointer. At operation 934, the write target is advanced by the size of the pointer. At operation 936, deserialization is entered recursively. Entering deserialization recursively writes a new structure starting at end of data. The size and format of the new structure is determined when the embedded object is received from the host computer 110 and parsed.

At operation 908, when it is determined that the end of data has been reached, the CRC of the object, for example CRC 408 is read. At operation 910, CRC 408 is compared with the CRC calculated during the processing of the object, as discussed in relation to operation 632. In addition, a layer of CRC processing is removed, indicating that the CRC of the object has been processed.

Figure 12:
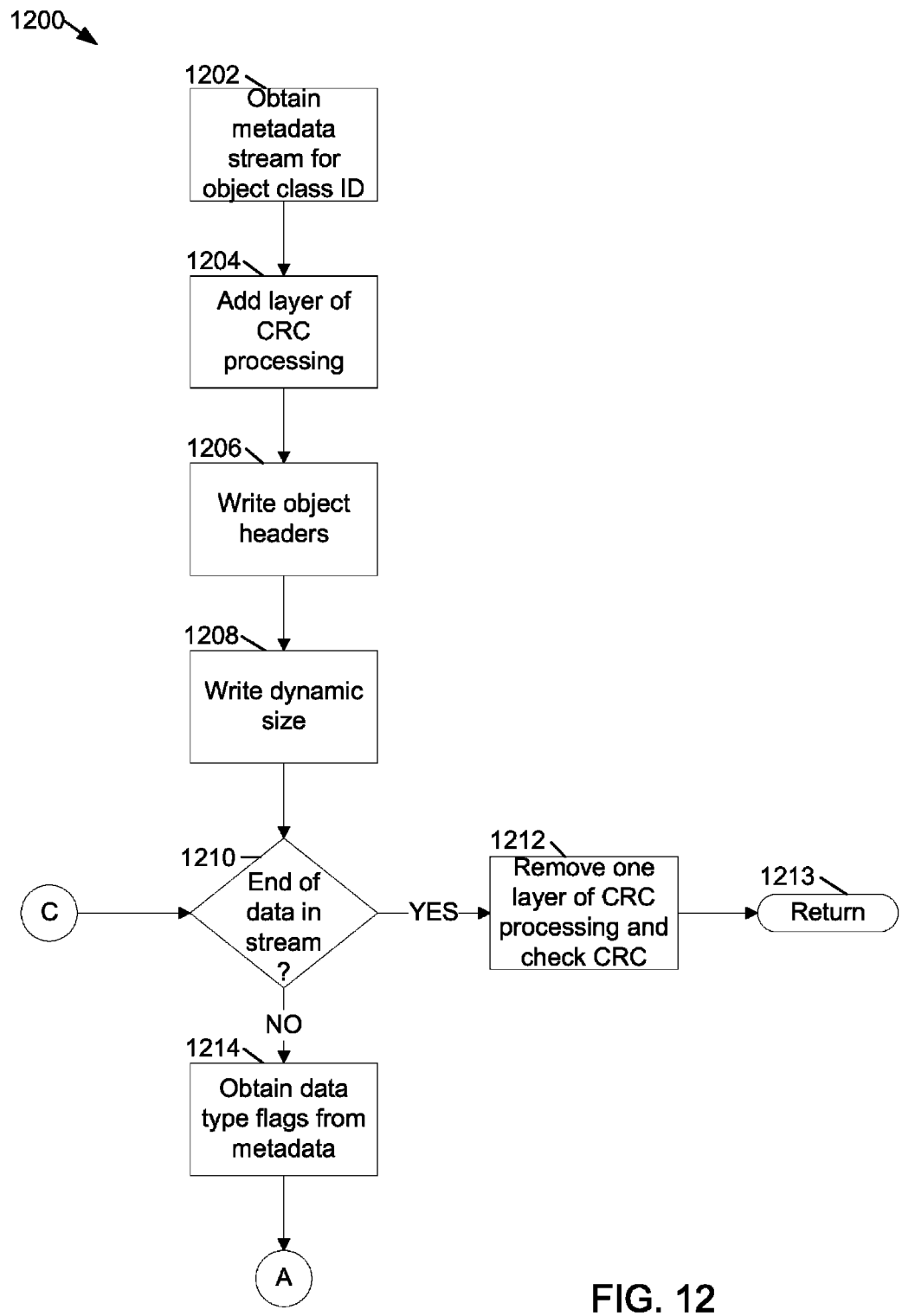
FIGS. 12, 13 and 14 show an example method for serializing metadata obtained from a medical sensor device.
Figure 13:
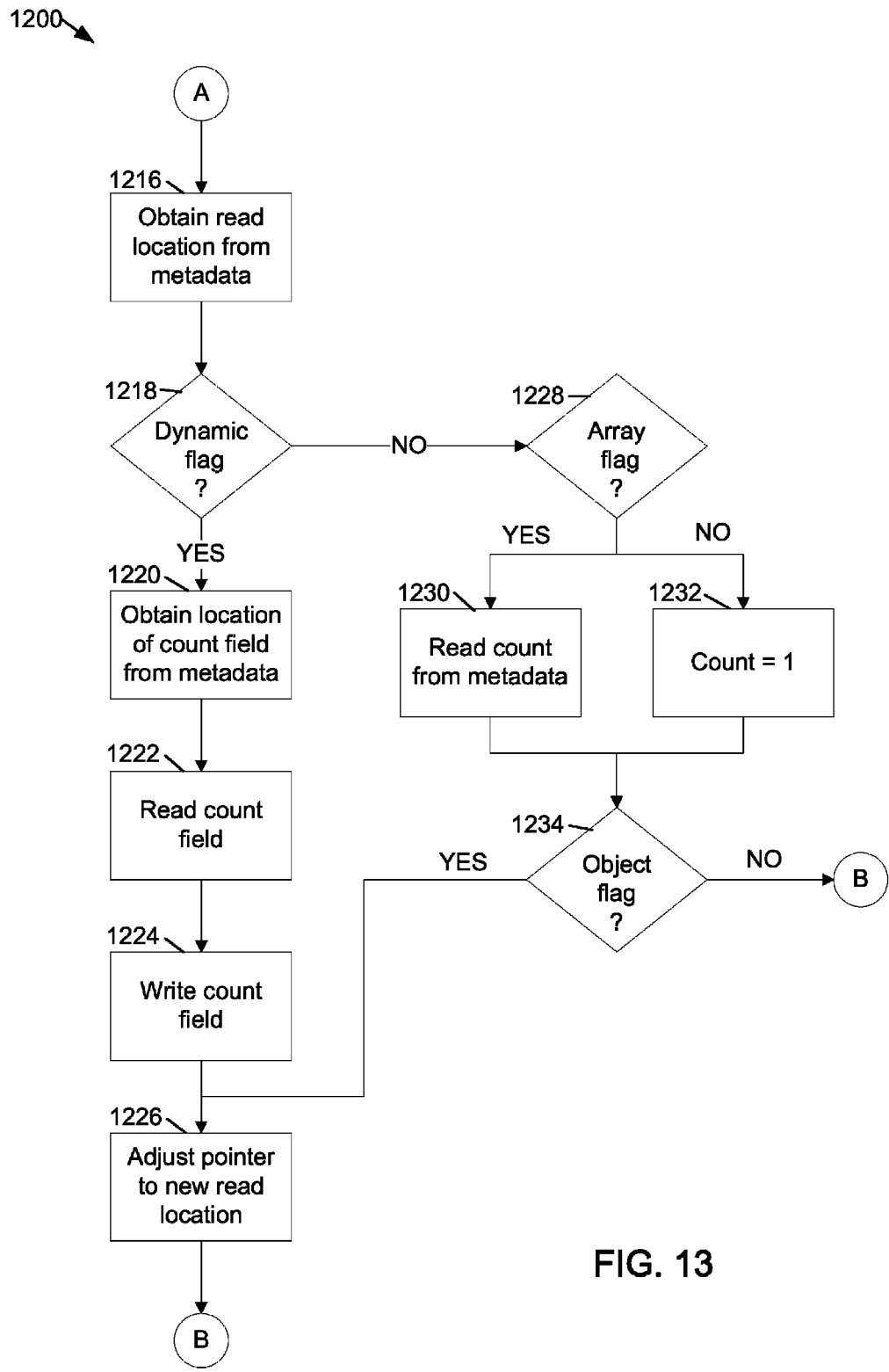
Figure 14:
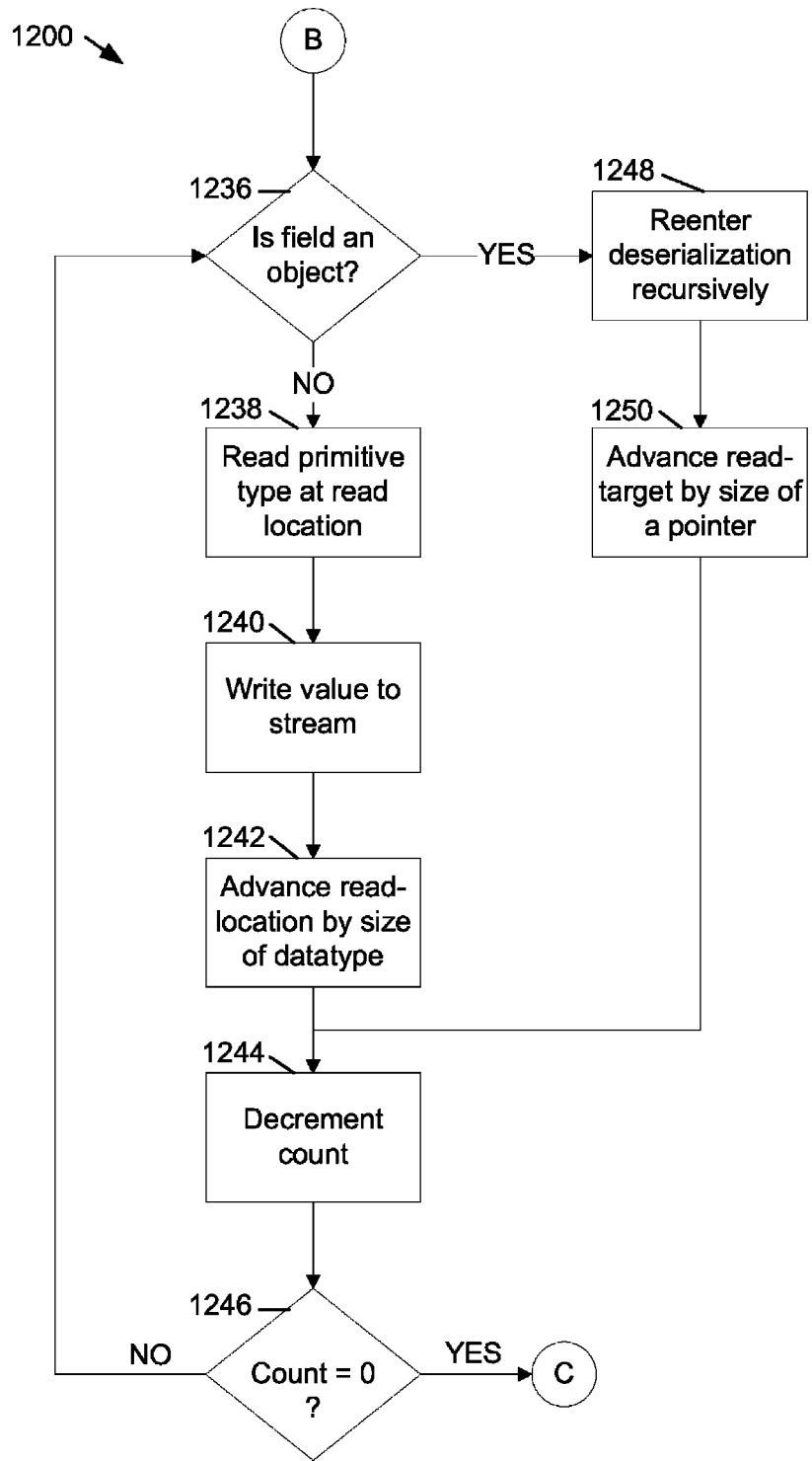

FIGS. 12, 13 and 14 show an example flow chart of a method 1200 for serializing data for an object, for example object 406. The intent of serializing the data is to insert data obtained from an application in a medical device, for example the temperature of the patient or blood pressure readings from the patient, into an object that can be interpreted by a host computer, for example by host computer 110. The data is stored in a buffer memory and serialized into a data stream to be sent to host computer 110.

At operation 1200, metadata is located on the medical device based on an object class ID. The metadata is generated once by an application program, typically run on a personal computer, and stored in metadata storage ROM 206 in a C programming language structure. The object class ID corresponds to an object, for example object 406, for which medical information is obtained on the medical device. The obtained medical information is stored in memory on the medical device.

For example, if a request was made to obtain the temperature of a patient using medical device 110, a software application on medical device 110 obtains the temperature and stores the temperature data according to example class ID 516. In this example, class ID 516 specifies temperature and also specifies data to be returned with the temperature. For example, temperature may be associated with object 406, wherein the temperature may be included as one or more static variables. As another example, the data stream in operation 1200 may represent blood pressure data from example medical device 104. This data stream typically includes dynamic data and may be associated with object 406, wherein the blood pressure readings may be included as one or more dynamic variables.

At operation 1204, a layer of CRC processing is added for the data in the stream. This layer of CRC processing calculates a CRC for the data in the stream. The CRC is calculated for each byte in the stream as it is received. When completed the CRC is inserted at the end of the object, for example as CRC 408.

At operation 1206, object headers are written for the data stream. The object headers reflect the structure of the data as determined by the object class ID. For example, the data stream may include static variables, dynamic variables or a combination of static and dynamic variables.

At operation 1208, a size measurement algorithm is run based on the object headers, the size of the dynamic data is determined and the dynamic data size is stored in memory, for example as dynamic size variable 630. At operation 1210, a determination is made as to whether the end of the data stream has been reached. When it is determined that the end of the data stream has not been reached, at operation 1214, data type flags are obtained from the metadata. For example, the data type flags may specify that the data type is an integer, 4-bytes in length.

At operation 1216, the read location is obtained from the metadata. The read location corresponds to the location in buffer memory from which a byte of obtained medical device information is to be read.

At operation 1218, a determination is made as to whether a dynamic flag is set in the metadata. When a determination is made that a dynamic flag is set, indicating that the obtained medical device information in buffer memory includes dynamic information, at operation 1220 the location of the count field is obtained from the buffer memory. The count field specifies the number of elements of dynamic information included in the buffer memory, for example the number of samples of a wave.

At operation 1222, the count field is read and at operation 1224, the count field is written to the data stream. The count field is written to the data stream immediately before the dynamic data, for example before the wave samples. At operation 1224, pointers are adjusted to a new read location. For example, the size of the dynamic data area is calculated based on the count and data type flags and read pointers are adjusted to point just past the end of the dynamic data area so that additional data can be obtained.

When it is determined at operation 1218 that a dynamic flag is not set, at operation 1228 a determination is made as to whether an array flag is set in the metadata. When it is determined that an array flag is set, at operation 1230, the read count is obtained from the metadata. When the array flag is set, the read count specifies the number of elements in an array, for example an array that stores a patient's name. When it is determined that an array flag is not set, at operation 1232, the count is set equal to 1.

At operation 1234, a determination is made as to whether an object flag is set. When it is determined that an object flag is set, at operation 1226, a read pointer is adjusted to a new read location. The read pointer is adjusted to point just past the object so that additional data can be read from the buffer memory.

At operation 1236, a determination is made whether the current field is an object. If the current field is not an object, at operation 1238, a primitive type is read from the current read location. A primitive type can be either a character or a number. At operation 1240, the primitive type is written to data stream. At operation 1242, the read location is advanced by the size of the data type, for example by 4-bytes for an integer and by one-byte for a character.

At operation 1244, the count set earlier is decremented by one. Then, at operation 1246, a determination is made as to whether the count is equal to zero. When a determination is made that the count is equal to zero, control proceeds to operation 1210, and if the end of data is not reached, another byte of packet data is processed. However, if a determination is made at operation 1246 that the count is not zero, control proceeds to operation 1236 and a determination is made whether the current field is an object. The count is not zero if there are more bytes of an array, more dynamic bytes or more embedded objects to process, as determined by the count read at operations 1230 and 1222 for arrays and dynamic elements, respectively. Typically, only one object is embedded.

At operation, 1236, when a determination is made that the field is an object, this is an indication of an object embedded inside another object. At operation 1248, serialization is entered recursively, starting at the target pointed to by the current read location. At operation 1250, the read location is advanced by the size of a pointer corresponding to an embedded object. At operation 1244, the count is decremented by one and at operation 1246 a determination is made whether the count is equal to zero. Control then passes to either operation 1210 or operation 1236 as discussed above.

At operation 1210, when it is determined that the end of data has been reached, the CRC of the object, for example CRC 408 is read. At operation 1210, CRC 408 is compared with the CRC calculated during the processing of the metadata stream, as discussed in relation to operation 632. In addition, a layer of CRC processing is removed, indicating that the CRC of the object has been processed.

The various embodiments described above are provided by way of illustration only and should not be construed to limiting. Various modifications and changes that may be made to the embodiments described above without departing from the true spirit and scope of the disclosure.

What is claimed is:

1. A method of communicating information from a host computer to a sensor device, the method comprising:

receiving a data stream from the host computer, the data stream including a plurality of bytes, one or more bytes of the plurality of bytes being associated with obtaining medical related information, one or more of the one or more bytes associated with obtaining medical related information including one or more named fields;

parsing one or more bytes in the data stream at the sensor device;

as a result of parsing the one or more bytes, identifying a type of medical related information;

obtaining the medical related information from the sensor device, the medical related information being obtained using the one or more named fields, the one or more named fields determining a format of the medical related information; and sending the medical related information to the host computer;

wherein the parsing of the one or more bytes in the data stream is performed using a single pass through the data stream, a data validity check being performed for each of an envelope section, a message section, and an object section of the data stream during the single pass through the data stream, the envelope section including a size of the envelope section, the message section and a cyclic redundancy check (CRC) field for the envelope section, the message section including a message class identifier that identifies a first class of medical information, the object section and a CRC field for the message section, the object section including an object class identifier that identifies a sub-class of the first class of medical information, an object data section and a CRC field for the object section, the medical related information being obtained after the data stream is parsed in the single pass through the data stream.

2. The method of claim 1, wherein the data stream includes a first section, a second section and a third section, the first section being the envelope section, the second section being the message section and the third section being the object section.

3. The method of claim 2, further comprising identifying one or more bytes in the first section, performing a cyclic redundancy check (CRC) calculation for the one or more bytes in the first section and storing the result of the CRC calculation in a first memory area on the sensor device, the result of the CRC calculation being a CRC for the one or more bytes.

4. The method of claim 3, further comprising:
identifying a start of the second section;
performing a CRC calculation for a first byte in the second section;
storing the result of the CRC calculation for the first byte in the second section in a second memory area on the sensor device, the result of the CRC calculation for the first byte in the second section being a CRC for the first byte in the second section;
updating the CRC for the first section to include the first byte in the second section; and
storing the updated CRC for the first section in the first memory area on the sensor device.

5. The method of claim 4, further comprising:
identifying one or more additional bytes in the second section;
updating the CRC for the second section to include the one or more additional bytes in the second section;
storing the updated CRC for the second section in the second memory area on the sensor device;
updating the CRC for the first section to include the one or more additional bytes in the second section; and
storing the updated CRC for the first section in the first memory area on the sensor device.

6. The method of claim 5, further comprising:
identifying a start of the third section;
performing a CRC calculation for a first byte in the third section;
storing the result of the CRC calculation for the first byte in the third section in a third memory area on the sensor device, the result of the CRC calculation being a CRC for the first byte in the third section;
updating the CRC for the first section to include the first byte in the third section; storing the updated CRC for the first section in the first memory area on the sensor device;
updating the CRC for the second section to include the first byte in the third section; and
storing the updated CRC for the second section in the second memory area on the sensor device.

7. The method of claim 6, further comprising:
identifying one or more additional bytes in the third section;
updating the CRC for the third section to include the one or more additional bytes in the third section;
storing the updated CRC for the third section in the third memory area on the sensor device;
updating the CRC for the first section to include the one or more additional bytes in the third section;
storing the updated CRC for the first section in the first memory area on the sensor device;
updating the CRC for the second section to include the one or more additional bytes in the third section; and
storing the updated CRC for the second section in the first memory area on the sensor device.

8. The method of claim 7, further comprising identifying a first CRC at the end of the third section, identifying a second CRC at the end of the second section and identifying a third CRC at the end of the first section.

9. The method of claim 8, further comprising determining whether the first CRC matches the value stored in the third memory area, determining whether the second CRC matches the value stored in the second memory area and determining whether the third CRC matches the value stored in the first memory area.

10. The method of claim 9, further comprising when the first CRC matches the value stored in the third memory area and when the second CRC matches the value stored in the second memory area and when the third CRC matches the value stored in the first memory area, processing actionable data bytes obtained from the data stream, the processing of the actionable data bytes obtained from the data stream identifying the medical related information to be obtained from the medical device.

11. The method of claim 2, further comprising storing each byte of the third section in a buffer memory, each byte of the third section being stored in a separate location of the buffer memory.

12. The method of claim 11, wherein data bytes from the second section and the contents of the buffer memory include actionable data that identifies the medical related information to be obtained from the sensor device.

13. A first computing device comprising a processing unit and system memory, the memory of the first computing device including instructions that, when executed by the processing unit cause the first computing device to:
receive a data stream that includes a plurality of bytes, one or more bytes of the plurality of bytes being associated with obtaining medical related information, one or more of the one or more bytes associated with obtaining medical related information including one or more named fields;
parse each byte of the data stream serially;
identify metadata relating to actionable data in the data stream;
use the metadata to determine where to store the actionable data on the first computing device;
after each byte of actionable data is parsed, store the parsed byte of actionable data in a buffer memory for actionable data on the first computing device, the parsed byte of actionable data being stored in the location of buffer memory indicated by the metadata; and
use the actionable data in the buffer memory to obtain medical data from a sensor at the first computing device, the medical data being obtained using the one or more named fields, the one or more named fields determining a format of the medical related information;
wherein the parsing of the plurality of bytes in the data stream is performed using a single pass through the data stream, a data validity check being performed for each of an envelope section, a message section, and an object section of the data stream during the single pass through the data stream, the envelope section including a size of the envelope section, the message section and a cyclic redundancy check (CRC) field for the envelope section, the message section including a message class identifier that identifies a first class of medical information, the object section and a CRC field for the message section, the object section including an object class identifier that identifies a sub-class of the first class of medical information, an object data section and a CRC field for the object section, the medical related information being obtained after the data stream is parsed in the single pass through the data stream.

14. The computing device of claim 13, wherein the data stream includes dynamic data, a count field being included in the data stream indicating a number of elements of dynamic data, the dynamic data being stored in locations in the buffer memory determined by the count field and a data type size for the dynamic data.

15. The computing device of claim 13, wherein the data stream includes an array, the size of the array being determined from the metadata.

16. The computing device of claim 13, wherein the data stream includes an object, the metadata including a pointer to the object, the object being stored in the buffer memory at a location determined by the pointer to the object.

17. The computing device of claim 13, wherein the object includes a second object embedded in the object.

18. The computing device of claim 13, wherein the metadata is based on a hardware configuration of the computing device.

\* \* \* \* \*